US011796536B2

(12) United States Patent
Karlsson (10) Patent No.: US 11,796,536 B2
(45) Date of Patent: Oct. 24, 2023

(54) METHOD FOR DETERMINING ANALYTE-LIGAND BINDING ON A SENSOR SURFACE (71) Applicant: CYTIVA SWEDEN AB, Uppsala (SE)

(72) Inventor: Olof Karlsson, Uppsala (SE)

(73) Assignee: Cytiva Sweden AB, Uppsala (SE)

( * ) Notice: Subject to any disclaimer, the term of this patent is extended or adjusted under 35 U.S.C. 154(b) by 616 days.

(21) Appl. No.: 16/932,453

(22) Filed: Jul. 17, 2020

(65) Prior Publication Data
US 2020/0348295 A1 Nov. 5, 2020

Related U.S. Application Data (62) Division of application No. 15/529,466, filed as application No. PCT/EP2015/077568 on Nov. 24, 2015, now Pat. No. 10,725,030.

(30) Foreign Application Priority Data

Nov. 28, 2014 (SE) .................................. 1451456-6

(51) Int. Cl.
G01N 33/543 (2006.01)
(52) U.S. Cl.
CPC . G01N 33/54373 (2013.01); G01N 33/54393 (2013.01)
(58) Field of Classification Search
CPC ....... G01N 33/54373; G01N 33/54393; G01N 33/558
See application file for complete search history.

(56) References Cited

U.S. PATENT DOCUMENTS 5,599,668 A * 2/1997 Stimpson ............. G01N 21/552 435/7.1
2001/0040130 A1 11/2001 Lorch et al.
2004/0235195 A1 11/2004 Wada et al.
2012/0321617 A1 12/2012 Osterroth et al.

FOREIGN PATENT DOCUMENTS

| EP | 27700580 | 8/2014 |
| EP | 1631824 B1 | 4/2018 |
| JP | 2004251807 A | 9/2004 |
| JP | 2006527365 A | 11/2006 |
| JP | 4316490 B2 | 8/2009 |
| JP | 2013511995 A | 4/2013 |
| WO | 9609532 A1 | 3/1996 |
| WO | 03091706 A1 | 11/2003 |
| WO | 20041092840 | 12/2004 |
| WO | 2015147915 A1 | 10/2015 |

OTHER PUBLICATIONS

Myszka et al. (Analysis of Fibril Elongation Using Surface Plasmon Resonance Biosensors. Methods in Enzymology 25: 386-402 (1999))—IDS.*
Office Action received in Japanese Application No. 2017-528219 dated Aug. 23, 2021, with translation, 15 pages.
"Biacore Assay Handbook," 29-0194-00 Edition M, GE Healthcare, May 2012, [online][retrieved] from http://www.gelifesciences.com/file_source/GELS/Service%20and%20Support/Documents%20and%20Downloads/Handbooks/pdfs/Biacore%20Assay%20Handbook.pdf; whole document.
"Fragment Library and Characterization with Biocore 4000," GE Healthcare, Application note 28-9796-95 AA, Jan. 1, 2011, [online][retrieved on May 25, 2015] from https://www.gelifesciences.eo.jp/technologies/biacore/pdf/L01_28-9796-95AA.pdf; whole document.
Olsson et al., "Theory and Application of Diffusion-Limited Amperometric Enzyme Electrode Detection in Flow Injection Analysis of Glucose," published in 1986.
China First Office Action corresponding to Chinese Application No. 201580074734.7, dated Mar. 6, 2019.
China Supplementary Search Report corresponding to Chinese Application No. 201580074734.7, dated Feb. 26, 2019.
Feng-Sheng et al., "Chip-Based Protein-Protein Interaction Studied by Atomic Force Microscopy," published on Apr. 26, 2012.
Giannetti "From Experimental Design to Validated Hits a Comprehensive Walk-Through of Fragment Lead Identification Using Surface Plasmon Resonance," Methods in Enzymology, vol. 493, Jan. 1, 2011; pp. 169-218.
International Search Report and Written Opinion for corresponding PCT application No. PCT/EP2015/07768, dated Feb. 8, 2016, 15 pages.
Japanese Office Action Application No. 2017-528219 dated Mar. 9, 2020, 3 pages.
M.A. Kalinina et al., "Langmuir-Blodgett Composite Films for the Selective Determination of Calcium in Aqueous Solutions," Russian Journal of Physical Chemistry A, col. 82, No. 8, Aug. 1, 2008; pp. 1334-1342.
McLaughlin et al.: "Quantitative Analysis of Mitoxantrone by Surface-Enhanced Resonance Raman Scattering," Analytical Chemistry, vol. 74, No. 13, Jul. 1, 2002; pp. 3160-3167.
Myszka D. G. et al., "Analysis of Fibril Elongation Using Surface Plasmon Resonance Biosensors," Methods in Enzymology, Academic Press, US, vol. 309, Jan. 1, 1999, pp. 386-402, XP008028557, (Year: 1999) (reference already provided by Applicant).
Notice of Opposition in Corresponding EP 15802025.5 (EP3224622).
SE International-Type Search Report for corresponding SE application No. 1451456-6 dated May 25, 2015; 5 pages.
Office Action received in Japanese Application No. 2020-191572 dated Jan. 4, 2022, with translation, 19 pages.

* cited by examiner

Primary Examiner — Gailene Gabel
(74) Attorney, Agent, or Firm — Jeff B. Vockrodt; Culhane Meadows PLLC (57) ABSTRACT The present invention provides a method of assaying a sample solution for the presence of a first analyte comprising: (a) providing a sensor surface having a ligand immobilized thereto; (b) flowing the sample solution over the sensor surface; and (c) detecting the presence or absence of binding of the analyte to the ligand on the sensor surface; wherein the contact time between the sample solution and the immobilized ligand is less than 15 seconds.

20 Claims, 5 Drawing Sheets

METHOD FOR DETERMINING ANALYTE-LIGAND BINDING ON A SENSOR SURFACE

CROSS REFERENCE TO REPLATED APPLICATIONS

This application is a divisional of U.S. patent application Ser. No. 15/529,466, filed May 24, 2017, which is a filing under 35 U.S.C. § 371 of international application number PCT/EP2015/077568, filed Nov. 24, 2015, which claims priority to application number SE 1451456-6 filed in Sweden on Nov. 28, 2014, the entire disclosures of each of which are hereby incorporated by reference.

FIELD OF THE INVENTION

The present invention relates to a method of determining molecular binding interactions at a sensor surface, and more particularly to a method of determining an interaction between an analyte and a ligand using a biosensor.

BACKGROUND TO THE INVENTION

Analytical sensor systems that can monitor interactions between molecules, such as biomolecules, in real time are gaining increasing interest. These systems are often based on optical biosensors and usually referred to as interaction analysis sensors or biospecific interaction analysis sensors. A representative such biosensor system is the BIACORE® instrumentation sold by GE Healthcare, which uses surface plasmon resonance (SPR) for detecting interactions between molecules in a sample and molecular structures immobilized on a sensing surface. As sample is passed over the sensor surface, the progress of binding directly reflects the rate at which the interaction occurs. Injection of sample is followed by a buffer flow during which the detector response reflects the rate of dissociation of the complex on the surface. A typical output from the BIACORE® system is a graph or curve describing the progress of the molecular interaction with time, including an association phase part and a dissociation phase part. This binding curve, which is usually displayed on a computer screen, is often referred to as a "sensorgram".

With the BIACORE® system (and analogous sensor systems) it is thus possible to determine in real time without the use of labeling, and often without purification of the substances involved, not only the presence and concentration of a particular molecule (analyte) in a sample, but also additional interaction parameters, including kinetic rate constants for binding (association) and dissociation in the molecular interaction as well as the affinity for the surface interaction. The association rate constant ($k_a$) and the dissociation rate constant ($k_d$) can be obtained by fitting the resulting kinetic data for a number of different sample analyte concentrations to mathematical descriptions of interaction models in the form of differential equations. The affinity (expressed as the affinity constant $K_A$ or the dissociation constant $K_D$) can be calculated from the association and dissociation rate constants. It is also possible to measure affinity values by equilibrium binding analysis, which involves determining, for a series of analyte concentrations, the level of binding at equilibrium, or steady state, which is presumed to have been reached at or near the end of the association phase of the binding interaction.

In the current approach, the methodology strives to obtain highly repeatable, high quality response signals. This is achieved by several time-consuming measures like long injection or contact times (greater than 30 seconds) to have high and stable response values; washing the fluidics system to avoid disturbances; carry-over control injections to monitor response contribution from pollutions of the fluidics; and regeneration to bring the sensor surface to the same start condition in every cycle. These steps can be very time consuming, and resulting cycle times can typically reach 600 seconds or more. Such long cycle times can lead to significant runtimes, particularly so where there is a need to assess multiple analyte samples in a single experiment.

The present invention at least partially aims to overcome the problems associated with current methods of assessing interactions between an analyte and a ligand using a biosensor.

SUMMARY OF THE INVENTION

According to a first aspect of the present invention, there is provided a method of assaying a sample solution for the presence of a first analyte comprising:
(a) providing a sensor surface having a ligand immobilized thereto;
(b) flowing the sample solution over the sensor surface; and
(c) detecting the presence or absence of binding of the analyte to the ligand on the sensor surface;
wherein the contact time between the sample solution and the immobilized ligand is less than 15 seconds.

The present application demonstrates that it is possible to provide meaningful and repeatable binding data relating to the binding of the surface-bound ligand and analyte whilst significantly reducing the contact time between the solution comprising the analyte and the ligand. As stated earlier, it is standard practice in the art to employ long injection or contact times (typically greater than 30 seconds) to ensure high and stable response values. However, the present inventor has identified that significantly reducing the contact time, for example to two seconds or below, still produces useful and repeatable information. This discovery provides significant advantages in the field of analyte analysis, for example in areas of drug discovery, including antibody screening, and fragment-based screening. In particular, reducing contact times can significantly enhance throughput. This can be enhanced further by eliminating further time consuming measures such as washing the fluidics system (employed to avoid disturbances), carry-over control injection to monitor response contributions from pollutions of the fluidics, and regeneration to bring the sensor surface to the same start condition in every cycle. For example, by using a sufficiently high density of ligand in combination with short contact time, the need to regenerate the surface can be eliminated since the ligand density ensures sufficient analyte binding, whilst providing enough free ligand to detect several samples after each other. This is possible since only a small fraction of the capacity is used for each binding and means that regeneration is not necessary for the typical number of binders in screening runs.

In one embodiment, the contact time is less than 10 seconds. In a further embodiment, the contact time is less than 5 seconds. In a further embodiment, the contact time is less than 3 seconds. In a further embodiment, the contact time is less than 2 seconds.

In a further embodiment, detection at the sensor surface is based on evanescent wave sensing.

In a further embodiment, detection at the sensor surface is based surface plasmon resonance (SPR).

In a further embodiment, following step (c), steps (b) and (c) are repeated by flowing a second sample solution over the surface to detect the presence or absence of the binding between ligand and a further analyte. The further analyte may be the same as the first analyte. Alternatively, the further analyte may be different to the first analyte. In a yet further embodiment, steps (b) and (c) are repeated for a third sample solution. In further embodiment, steps (b) and (c) are repeated at least ten times to assay at least ten further solutions.

In a further embodiment, the time between initiating flowing of at least one of the sample solutions over the sensor surface and initiating flowing of a next sequential sample solution over the sensor surface (cycle time) is less than 40 seconds. In a further embodiment, the cycle time is less than 15 seconds.

In a further embodiment, no regeneration step is carried out between initiating the flowing of at least one of the sample solutions over the sensor surface and initiating flowing of a next sequential sample solution over the sensor surface.

In a further embodiment, no washing step and/or no carry-over control injection step is carried out between initiating the flowing of at least one of the sample solutions over the sensor surface and initiating flowing of a next sequential sample solution over the sensor surface.

In a further embodiment, the ligand density on the sensor surface is up to 50000 RU. In a further embodiment, the ligand density on the sensor surface is in the range 5000 RU to 15000 RU.

In a further embodiment, step (c) comprises determining the analyte concentration in the sample solution.

In a further embodiment, step (c) comprises determining the affinity of analyte to the ligand.

In a further embodiment, the method comprises determining differences (relative or absolute) in analyte concentrations and/or analyte affinities between different sample solutions.

In a further embodiment, the ligand or analyte is an antibody or fragment thereof. In a further embodiment, the method is used to screen antibodies.

In a further embodiment, the method is used as a fragment-based screen to identify non-specific binders or aggregators.

In a further embodiment, the method is used as a fragment-based screen to identify specific binders to the ligand.

According to a second aspect of the present invention, there is provided a computer program comprising program code means for operating a sensor device to detect an interaction between an analyte and a ligand on a sensor surface according to a method comprising (a) providing a sensor surface having a ligand immobilized thereto;
(b) flowing the sample solution over the sensor surface; and
(c) detecting the presence or absence of binding of the analyte to the ligand on the sensor surface; wherein the contact time between the sample solution and the immobilized ligand is less than 15 seconds; and wherein the program is run on a computer. The method may have the features described in any of the embodiments described above with respect to the first aspect of the present invention.

BRIEF DESCRIPTION OF THE DRAWING

FIG. 3 and FIG. 4 show the results of an experiment performed on a Biacore T200 instrument demonstrating the interaction between ligand (Anti-β2μ) at various concentrations of analyte (β2μ-globulin) employing a 2 second contact time.

DETAILED DESCRIPTION OF THE INVENTION

As mentioned above, in a first aspect, the present invention relates to a method of assaying a sample solution for the presence of a first analyte comprising: (a) providing a sensor surface having a ligand immobilized thereto; (b) flowing the sample solution over the sensor surface; and (c) detecting the presence or absence of binding of the analyte to the ligand on the sensor surface; wherein the contact time between the sample solution and the immobilized ligand is less than 15 seconds. Typically, the experimental binding data is obtained by sensor-based technology, which studies the molecular interactions and presents the results in real time as the interactions progress. Before describing the present invention in more detail, however, the general context in which the invention is intended to be used will be described.

Unless defined otherwise, all technical and scientific terms used herein have the same meaning as commonly understood by a person skilled in the art related to this invention. Also, the singular forms "a", "an", and "the" are meant to include plural reference unless it is stated otherwise.

All publications, patent applications, patents, and other references mentioned herein are incorporated by reference in their entirety.

Chemical sensors or biosensors are typically based on label-free techniques, detecting a change in a property of a sensor surface, such as e.g. mass, refractive index, or thickness for the immobilised layer, but there are also sensors relying on some kind of labelling. Typical sensor detection techniques include, but are not limited to, mass detection methods, such as optical, thermo-optical and piezoelectric or acoustic wave methods (including e.g. surface acoustic wave (SAW) and quartz crystal microbalance (QCM) methods), and electrochemical methods, such as potentiometric, conductometric, amperometric and capacitance/impedance methods. With regard to optical detection methods, representative methods include those that detect mass surface concentration, such as reflection-optical methods, including both external and internal reflection methods, which are angle, wavelength, polarization, or phase resolved, for example evanescent wave ellipsometry and evanescent wave spectroscopy (EWS, or Internal Reflection Spectroscopy), both of which may include evanescent field enhancement via surface plasmon resonance (SPR), Brewster angle refractometry, bio-layer interferometry (BLI), critical angle refractometry, frustrated total reflection (FTR), scattered total internal reflection (STIR) (which may include scatter enhancing labels), optical wave guide sensors; external reflection imaging, evanescent wave-based imaging such as critical angle resolved imaging, Brewster angle resolved imaging, SPR-angle resolved imaging, and the like. Further, photometric and imaging/microscopy methods, "per se" or combined with reflection methods, based on for example surface enhanced Raman spectroscopy (SERS), surface enhanced resonance Raman spectroscopy (SERRS), evanescent wave fluorescence (TIRF) and phosphorescence may be mentioned, as well as waveguide interferometers, waveguide leaky mode spectroscopy, reflective interference spectroscopy (RIfS), transmission interferometry, holographic spectroscopy, and atomic force microscopy (AFR).

Commercially available biosensors include the aforementioned BIACORE® system instruments, manufactured and marketed by GE Healthcare, Uppsala, Sweden, which are based on surface plasmon resonance (SPR) and permit monitoring of surface binding interactions in real time between a bound ligand and an analyte of interest. In this context, "ligand" is a molecule that has a known or unknown affinity for a given analyte and includes any capturing or catching agent immobilized on the surface, whereas "analyte" includes any specific binding partner thereto.

Typical ligands that can be used in the present invention include, but are not limited to, proteins (e.g., antibodies, affibodies, or aptamers), enzymes, receptors, antigens, haptens, peptides, or chemical molecules (e.g. drug candidates or fragments thereof).

Typical analytes that can be used in the present invention include, but are not limited to, proteins and glycoproteins (e.g., antibodies or fragments thereof, affibodies, or aptamers), lipids, carbohydrates, enzymes, receptors, antigens, haptens, peptides, or chemical molecules (e.g. drug candidates or fragments thereof, specific or non-specific binders, chelators or aggregators).

The term "antibody" describes an immunoglobulin whether natural or partly or wholly synthetically produced. The antibody may be monoclonal or polyclonal and may be prepared by techniques that are well-known in the art such as immunization of a host and collection of sera (polyclonal), or by preparing continuous hybrid cell lines and collecting the secreted protein (monoclonal), or by cloning and expressing nucleotide sequences or mutagenized versions thereof, coding at least for the amino acid sequences required for specific binding of natural antibodies. The term "antibody" also covers any polypeptide or protein comprising an antibody antigen-binding site. Antibody fragments that comprise an antibody antigen-binding site include, but are not limited to molecules such as Fab, Fab', Fab'-SH, scFv, Fv, dAb, Fd; and diabodies.

Methods of generating sensing surfaces for use in biosensor systems are well known in the art. Multiple examples of such methods are set out, for example, in U.S. Pat. Nos. 5,492,840 and 5,242,828, the contents of which are incorporated herein by reference.

While in the detailed description and Examples that follow, the present invention is illustrated in the context of SPR spectroscopy, and more particularly the BIACORE® system, it is to be understood that the present invention is not limited to this detection method. Rather, any affinity-based detection method where an analyte binds to a ligand immobilised on a sensing surface may be employed, provided that a change at the sensing surface can be measured which is quantitatively indicative of binding of the analyte to the immobilised ligand thereon.

The phenomenon of SPR is well known, suffice it to say that SPR arises when light is reflected under certain conditions at the interface between two media of different refractive indices, and the interface is coated by a metal film, typically silver or gold. In the BIACORE® instruments, the media are the sample and the glass of a sensor chip, which is contacted with the sample by a microfluidic flow system. The metal film is a thin layer of gold on the chip surface. SPR causes a reduction in the intensity of the reflected light at a specific angle of reflection. This angle of minimum reflected light intensity varies with the refractive index close to the surface on the side opposite from the reflected light, in the BIACORE® system the sample side.

Figure 1:
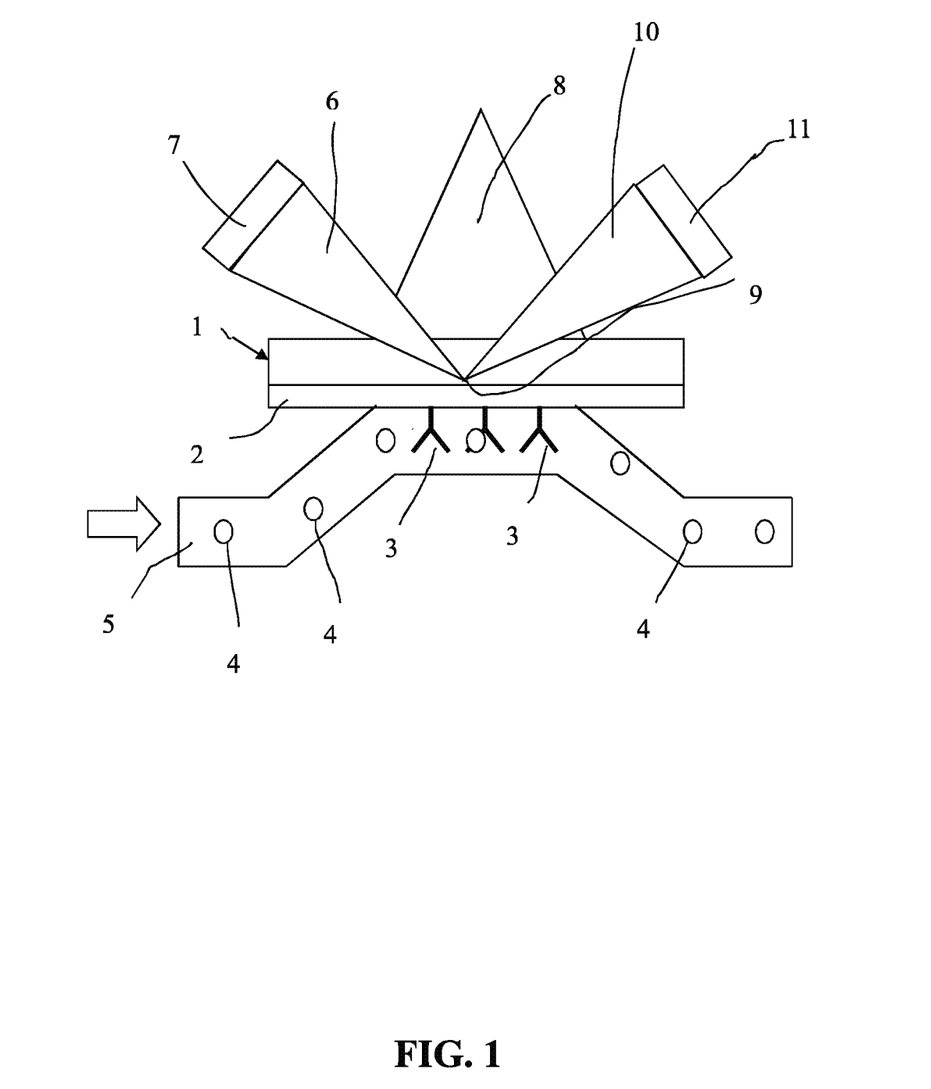
FIG. 1 is a schematic side view of a biosensor system based on SPR.

A schematic illustration of the BIACORE® system is shown in FIG. 1. Sensor chip 1 has a gold film 2 supporting capturing molecules (ligands) 3, e.g. antibodies, exposed to a sample flow with analytes 4, e.g. an antigen, through a flow channel 5. Monochromatic p-polarised light 6 from a light source 7 (LED) is coupled by a prism 8 to the glass/metal interface 9 where the light is totally reflected. The intensity of the reflected light beam 10 is detected by an optical detection unit 11 (photodetector array).

A detailed discussion of the technical aspects of the BIACORE® instruments and the phenomenon of SPR may be found in U.S. Pat. No. 5,313,264. More detailed information on matrix coatings for biosensor sensing surfaces is given in, for example, U.S. Pat. Nos. 5,242,828 and 5,436,161. In addition, a detailed discussion of the technical aspects of the biosensor chips used in connection with the BIACORE® instruments may be found in U.S. Pat. No. 5,492,840.

When molecules in the sample bind to the capturing molecules on the sensor chip surface, the concentration, and therefore the refractive index at the surface changes and an SPR response is detected. Plotting the response against time during the course of an interaction will provide a quantitative measure of the progress of the interaction. Such a plot, or kinetic or binding curve (binding isotherm), is usually called a sensorgram, also sometimes referred to in the art as "affinity trace" or "affinogram". In the BIACORE® system, the SPR response values are expressed in resonance units (RU). One RU represents a change of 0.0001° in the angle of minimum reflected light intensity, which for most proteins and other biomolecules correspond to a change in concentration of about 1 pg/mm$^2$ on the sensor surface. As sample containing an analyte contacts the sensor surface, the capturing molecule (ligand) bound to the sensor surface interacts with the analyte in a step referred to as "association." This step is indicated on the sensorgram by an increase in RU as the sample is initially brought into contact with the sensor surface. Conversely, "dissociation" normally occurs when the sample flow is replaced by, for example, a buffer flow. This step is indicated on the sensorgram by a drop in RU over time as analyte dissociates from the surface-bound ligand.

Figure 2:
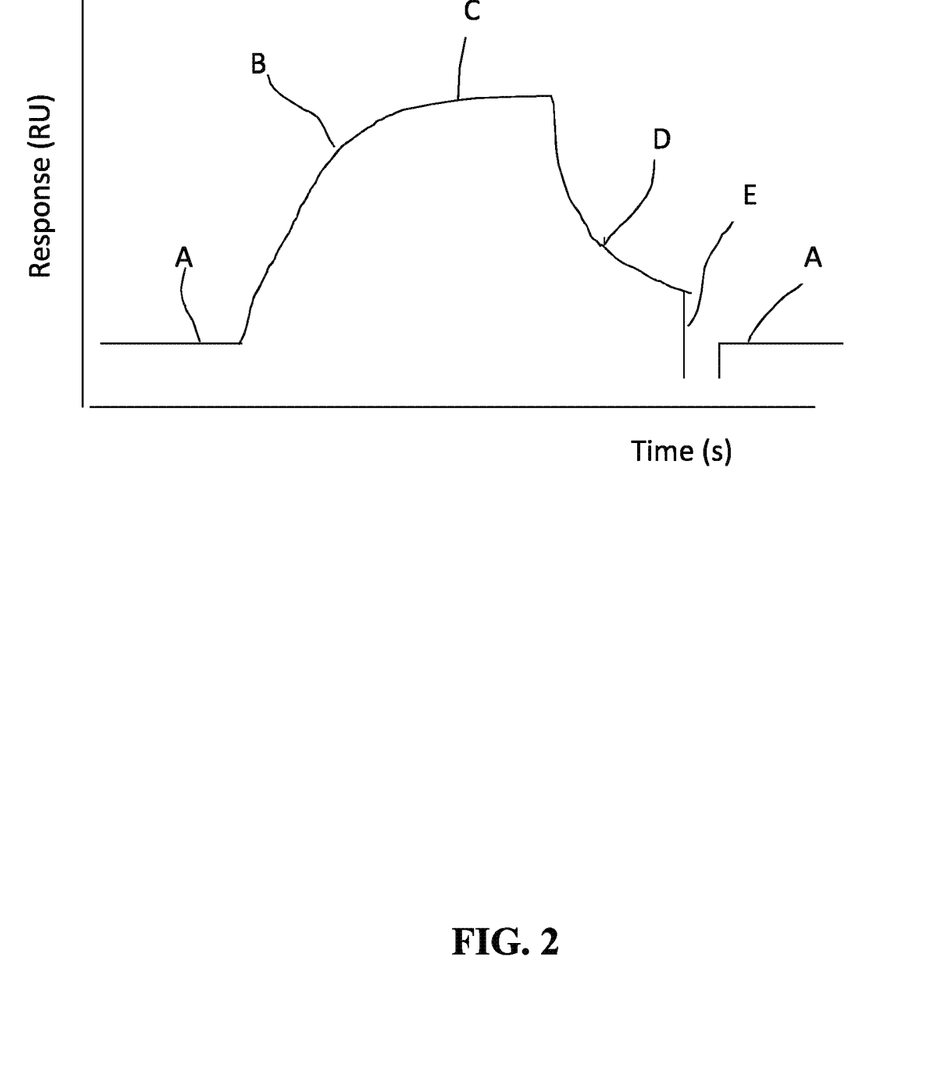
FIG. 2 is a representative sensogram showing detector response versus time for the interaction between an analyte and an immobilized binder for the analyte.

A representative sensorgram (binding curve) for a reversible interaction at the sensor chip surface is presented in FIG. 2, the sensing surface having an immobilised capturing molecule, or ligand, for example an antibody, interacting with a binding partner therefore, or analyte, in a sample. The binding curves produced by biosensor systems based on other detection principles mentioned above will have a similar appearance. The vertical axis (y-axis) indicates the response (here in resonance units, RU) and the horizontal axis (x-axis) indicates the time (here in seconds). Initially, buffer is passed over the sensing surface giving the baseline response A in the sensorgram. During sample injection, an increase in signal is observed due to binding of the analyte. This part B of the binding curve is usually referred to as the "association phase". Eventually, a steady state condition is reached at or near the end of the association phase where the resonance signal plateaus at C (this state may, however, not always be achieved). It is to be noted that herein the term "steady state" is used synonymously with the term "equilibrium" (in other contexts the term "equilibrium" may be reserved to describe the ideal interaction model, since in practice binding could be constant over time even if a system is not in equilibrium). At the end of sample injection, the sample is replaced with a continuous flow of buffer and a decrease in signal reflects the dissociation, or release, of analyte from the surface. This part D of the binding curve is usually referred to as the "dissociation phase". The analysis is ended by a regeneration step where a solution capable of removing bound analyte from the surface, while (ideally) maintaining the activity of the ligand, is injected over the sensor surface. This is indicated in part E of the sensorgram. However, regeneration can be avoided where dissociation is already complete or is expected to become completed before the next analysis, which has the advantage of enhancing ligand preservation and reducing the number of operations. Injection of buffer restores the baseline A and the surface is now ready for a new analysis.

From the profiles of the association and dissociation phases B and D, respectively, information regarding the binding and dissociation kinetics is obtained, and the height of the resonance signal at C represents affinity (the response resulting from an interaction being related to the change in mass concentration on the surface). A detailed explanation of methods used to determine parameters such as surface binding rates, kinetic rate constants ka and kd, affinity constants (association constant $K_A$ and dissociation constant $K_D$), and other parameters, is disclosed in US2012/0244637 A1.

Software for the analysis of kinetic and affinity data is commercially available. Thus, for example, evaluation of kinetic and affinity data produced by the BIACORE® instruments is usually performed with the dedicated BIAevaluation software (supplied by Biacore AB, Uppsala, Sweden) using numerical integration to calculate the differential rate equations and non-linear regression to fit the kinetic and affinity parameters by finding values for the variables that give the closest fit, reducing the sum of squared residuals to a minimum.

Determining affinity constants from measured steady state binding levels with the BIAevaluation software may, for example, involve the following steps:

(i) obtain steady state binding levels ($R_{eq}$, response at equilibrium) from report points on the sensorgrams in the steady state region of the curve;

(ii) create a plot of $R_{eq}$ against C, where C is the initial, or bulk, concentration of free analyte in solution; and (iii) fit this plot to a general "Steady state affinity" fitting model to obtain $K_A/K_D$ and $R_{max}$ (where $R_{max}$ is the response, in RU, obtained if analyte had bound to all ligand on the surface, also referred to as saturation response).

Contact Time

According to the first aspect of the invention, the contact time between the sample solution and the immobilized ligand is less than 15 seconds. The term "contact time" is well known in the art and, as used herein, means the total time that it takes the sample solution to flow over any one fixed point of the ligand-bound sensor surface. For example, the time can be determined from the start time from when the first part of the detection surface is contacted by the sample solution to the stop time when the first part of the surface is contacted with a following buffer solution.

Biosensor devices (such as, but not limited to the BIACORE® system) permit a user to set a preferred contact time. For example, by specifying a particular contact time and flow rate, PC software can calculate the appropriate sample volume which then, via the instrument software, executes the volume at the specified flow rate. For example, if the contact time is set at 2 seconds and the flow rate at 60 µl/min, a sample volume of 60/60×2=2 µl could be employed.

The present application demonstrates that it is possible to provide meaningful binding data relating to the binding of the surface-bound ligand and analyte whilst significantly reducing the contact time between the solution comprising the analyte and the ligand. As stated earlier, it is standard practice in the art to employ long injection or contact times (typically greater than 30 seconds) to ensure high and stable response values. However, the present inventor has identified that significantly reducing the contact time still produces useful and repeatable information. For example, the contact time may be below 15 seconds, below 14 seconds, below 13 seconds, below 12 seconds, below 11 seconds, below 10 seconds, below 9 seconds, below 8 seconds, below 7 seconds, below 6 seconds, below 5 seconds, below 4 seconds, below 3 seconds, below 2 seconds, or below 1 second. The contact time may be in the range 15 seconds to 2 seconds, 14 seconds to 2 seconds, 13 seconds to 2 seconds, 12 seconds to 2 seconds, 11 seconds to 2 seconds, 10 seconds to 2 seconds, 9 seconds to 2 seconds, 8 seconds to 2 seconds, 7 seconds to 2 seconds, 6 seconds to 2 seconds, 5 seconds to 2 seconds, 4 seconds to 2 seconds, 3 seconds to 2 seconds, or about 2 seconds. The contact time may be in the range 3 seconds to 0.1 seconds, 3 seconds to 0.2 seconds, 3 seconds to 0.3 seconds, 3 seconds to 0.4 seconds, 3 seconds to 0.5 seconds, 3 seconds to 0.6 seconds, 3 seconds to 0.7 seconds, 3 seconds to 0.8 seconds, 3 seconds to 0.9 seconds, 3 seconds to 1 second. The lower limit on the contact time may be 0.1 seconds, 0.2 seconds, 0.3 seconds, 0.4 seconds, 0.5 seconds, 0.6 seconds, 0.7 seconds, 0.8 seconds, 0.9 seconds, 0.1 seconds, 1 second, 1.1 seconds, 1.2 seconds, 1.3 seconds, 1.4 seconds, 1.5 seconds, 1.6 seconds, 1.7 seconds, 1.8 seconds, 1.9 seconds, or 2 seconds.

The discovery that significantly such low contact times can be used in a method according to the present invention provides significant advantages in the field of analyte analysis, for example in areas of drug discovery, including antibody screening, and fragment-based screening (described in more detail below). For example, reducing contact times can lead to faster results and can significantly enhance throughput by reducing cycle times.

In a further embodiment, following step (c), steps (b) and (c) are repeated over the same surface by flowing a second sample solution over the surface to detect the presence or absence of the binding between ligand and a further analyte. The further analyte may be the same as the first analyte. Alternatively, the further analyte may be different to the first analyte. Steps (b) and (c) may then be repeated for a third sample solution. In further embodiment, steps (b) and (c) are repeated at least two, three, four, five, six, seven, eight, nice, ten, eleven twelve, thirteen, fourteen, fifteen, sixteen, seventeen, eighteen, nineteen, or twenty times to assay the corresponding number of further solutions.

In a further embodiment, the time between initiating (e.g. injecting) flowing of at least one of the sample solutions over the sensor surface and initiating flowing of a next sequential sample solution over the sensor surface (cycle time) is less than 40 seconds. In a further embodiment, the cycle time is less than 30 seconds. In a further embodiment, the cycle time is less than 20 seconds. In a further embodiment, the cycle time is less than 15 seconds. In a further embodiment, the cycle time is less than 10 seconds. In a further embodiment, the cycle time is in the range of 10 seconds to 40 seconds, preferably in the range of 10 seconds to 30 seconds.

In a further embodiment, the time between initiating (e.g. injecting) flowing of each of the sample solutions over the sensor surface and initiating flowing of a next sequential sample solution over the sensor surface (cycle time) is less than 40 seconds. In a further embodiment, each cycle time is less than 30 seconds. In a further embodiment, each cycle time is less than 20 seconds. In a further embodiment, each cycle time is less than 15 seconds. In a further embodiment, each cycle time is less than 10 seconds. In a further embodiment, each cycle time is in the range of 10 seconds to 40 seconds, preferably in the range of 10 seconds to 30 seconds.

The cycle time between analyte solutions can be further reduced by eliminating further time consuming measures that are typically employed in biosensor-based analyte binding techniques, for example, washing the fluidics system, carry-over control and/or regeneration. As demonstrated in the Examples of the present application, useful and repeatable binding data was obtained for multiple analyte-biding cycles without employing such washing, carry-over control or regeneration steps.

Washing steps are typically carried out to ensure that there are not left over analytes stuck to the fluidics system which may contribute to disturbances in the binding data.

Carry-over control is a typical step administered to address the fact that some analytes are "sticky" and can be difficult to wash out of the fluidic system, causing "carry-over" of material to the next analysis cycle. This can be detected by routinely including a "carry-over injection" of buffer after the sample injection: the response from a "sticky" compound will be carried over into this buffer injection. Thus, a carry-over control injection can monitor response contribution from pollutions of the fluidics system.

Regeneration is the process of removing bound analyte from the surface after an analysis cycle without damaging the ligand, in preparation for a new cycle. Regeneration techniques are well known in the art, and the specific method employed may vary depending on the ligand and/or analyte employed. For assay development using custom antibodies, regeneration at low pH (glycine-HCl, pH 1.5 to 3) is usually effective.

In one embodiment of the present invention, no washing step is carried out between initiating the flowing of at least one of the sample solutions over the sensor surface and initiating flowing of a next sequential sample solution over the sensor surface.

In one embodiment, no carry-over control injection step is carried out between initiating the flowing of at least one of the sample solutions over the sensor surface and initiating flowing of a next sequential sample solution over the sensor surface.

In one embodiment, no regeneration step is carried out between initiating the flowing of at least one of the sample solutions over the sensor surface and initiating flowing of a next sequential sample solution over the sensor surface.

In one embodiment, no regeneration step and no carry-over control and/or system washing step is carried out between initiating the flowing of at least one of the sample solutions over the sensor surface and initiating flowing of a next sequential sample solution over the sensor surface.

In one embodiment, no regeneration step and/or no carry-over control and/or no system washing step is carried out between initiating the flowing of the first sample solution over the sensor surface and initiating flowing of each subsequent sample solution over the sensor surface.

The use of short contact times and avoiding the application of a regeneration step can be enhanced by employing a high density of immobilized ligand. A high density of ligand can maximise the amount of analyte that can contact the ligand, which can be particularly advantageous where the contact time (and hence time available for binding) is short, thus ensuring a good level of ligand-analyte binding. Furthermore, by employing a high density of ligand, in combination with a short contact time, only a small fraction of the sensor capacity (available binding sites for the analyte) is used for each analyte injection, thereby circumventing the requirement for regeneration.

In an embodiment of the present invention, the ligand density on the sensor surface is up to 50000 RU. In a further embodiment, the ligand density on the sensor surface is in the range 5000 RU to 15000 RU. These numbers are particularly preferred where the immobilised ligand is an antibody. Taking the typical approximate molecular weight of an antibody to be 150000 g/mole for other molecules with molecular weight X the immobilization level has to be calculated:

$$\text{New } immob \text{ level} = \frac{Ab \; immob \text{ level} \times X}{150000}$$

However, the choice of ligand density can also depend on the analyte, and in particular the molecular weight ratio of the ligand and analyte.

In a further embodiment, step (c) comprises determining the analyte concentration in the sample solution. In a further embodiment, step (c) comprises determining the affinity (e.g. binding constants) of analyte to the ligand.

However, the use of short contact times and/or short cycle times as described above means that that the present method is particularly advantageous in methods where large numbers of sample analyte solutions need to be assayed for ligand binding over short or more manageable periods of time. In this way, the user can e.g. quickly determine the presence or absence of analyte in a given sample solution, or e.g. determine qualitative or quantitative differences in analyte concentrations and/or analyte affinities between difference sample solutions. For example, the level of response can be used to draw conclusions regarding the relative affinity of the antibodies and/or the concentration of the antibody.

In a preferred embodiment of the present invention, the ligand or analyte is an antibody or fragment thereof. For example, the ligand may be an antibody, and the analyte may be a molecule capable of (or considered to be potentially capable of) binding to the antibody. Alternatively, the ligand may be a molecule capable of binding to a target antibody (e.g. an antigen), and the analyte solutions may comprise candidate antibodies that are capable of binding (or are to be tested for their ability to bind) the ligand. In this way, the method of the invention may be employed in antibody screening programs e.g. primary screens, to test different hybridomas (present e.g. on a 384-well plate) for their ability to bind the target antigen (ligand). Those that show binding in the assay of the present invention (by elevation of response signal) can be identified as producing an antibody that binds the target antigen. Furthermore, the level of response can be used to draw conclusions regarding the relative affinity of the antibodies and/or the concentration of the antibody.

The method of the present invention can also be advantageously employed in a fragment-based screen to identify non-specific binders or aggregators. Fragment-based drug discovery is a powerful method for discovering high-affinity binders for e.g. target proteins. Although there is no strict size requirement in order for a compound to be designated as a "fragment", the term is customarily used for small organic molecules with less than about 25 heavy atoms, or a molecular weight of less than 300 Da. However, before beginning a fragment-based screen, it is important to remove fragments that may misbehave, as the presence of such molecules can obscure or disturb the screening results. Such a screen is sometimes referred to as a "Clean-Screen", and is the recommended first step in a fragment screening campaign. Such "misbehaving" molecules can include non-specific binders, chelators or aggregators. Sorting out such misbehaving molecules can be a challenging task as not all such compounds are known in advance of the screen. However, the method of the present invention can be used to effectively "pre-screen" a fragment library for such misbehaving molecules. These can be identified by monitoring the signal associated with the binding of the molecules. For example, such molecules would be identifiable due to their slow dissociation due to their unwanted binding interactions. The method of the present invention may then be further used to screen the optimized fragment-based library.

According to a second aspect of the present invention, there is provided a computer program comprising program code means for operating a sensor device to detect an interaction between an analyte and a ligand on a sensor surface according to a method comprising (a) providing a sensor surface having a ligand immobilized thereto; (b) flowing the sample solution over the sensor surface; and (c) detecting the presence or absence of binding of the analyte to the ligand on the sensor surface; wherein the contact time between the sample solution and the immobilized ligand is less than 15 seconds; and wherein the program is run on a computer. The method may have the features described in any of the embodiments described above with respect to the first aspect of the present invention.

The present invention will now be described with reference to the following non-limiting examples.

EXAMPLES

Ultra High Biosensor Throughput
1. The ligand Anti-β2μ from GE Healthcare was diluted from 1 mg/ml stock solution to 30 μg/ml with 10 mM Acetate pH 5.0.
2. The ligand was amine coupled to Sensor chip CM7 by preprogrammed setting in the Biacore T200 system using the reagents in the Amine coupling kit from GE Healthcare. The ligand solution was injected for 7 min resulting in an immobilization level of 43319 RU. Running buffer: HBS-EP+ from GE Healthcare.
3. The analyte β2μ stock from GE Healthcare was diluted from 100 μg/ml to 1600 ng/ml with running buffer and then further to 800, 400, 200 & 100 ng/ml.
4. Each analyte concentration was injected 10 times with a contact time of 2 s at a flow rate 60 μl/min, going from low to high concentration. Between the different concentrations the chip was regenerated by a 30 s injection of 10 mM glycin pH 2.5 from GE Healthcare.

Figure 3:
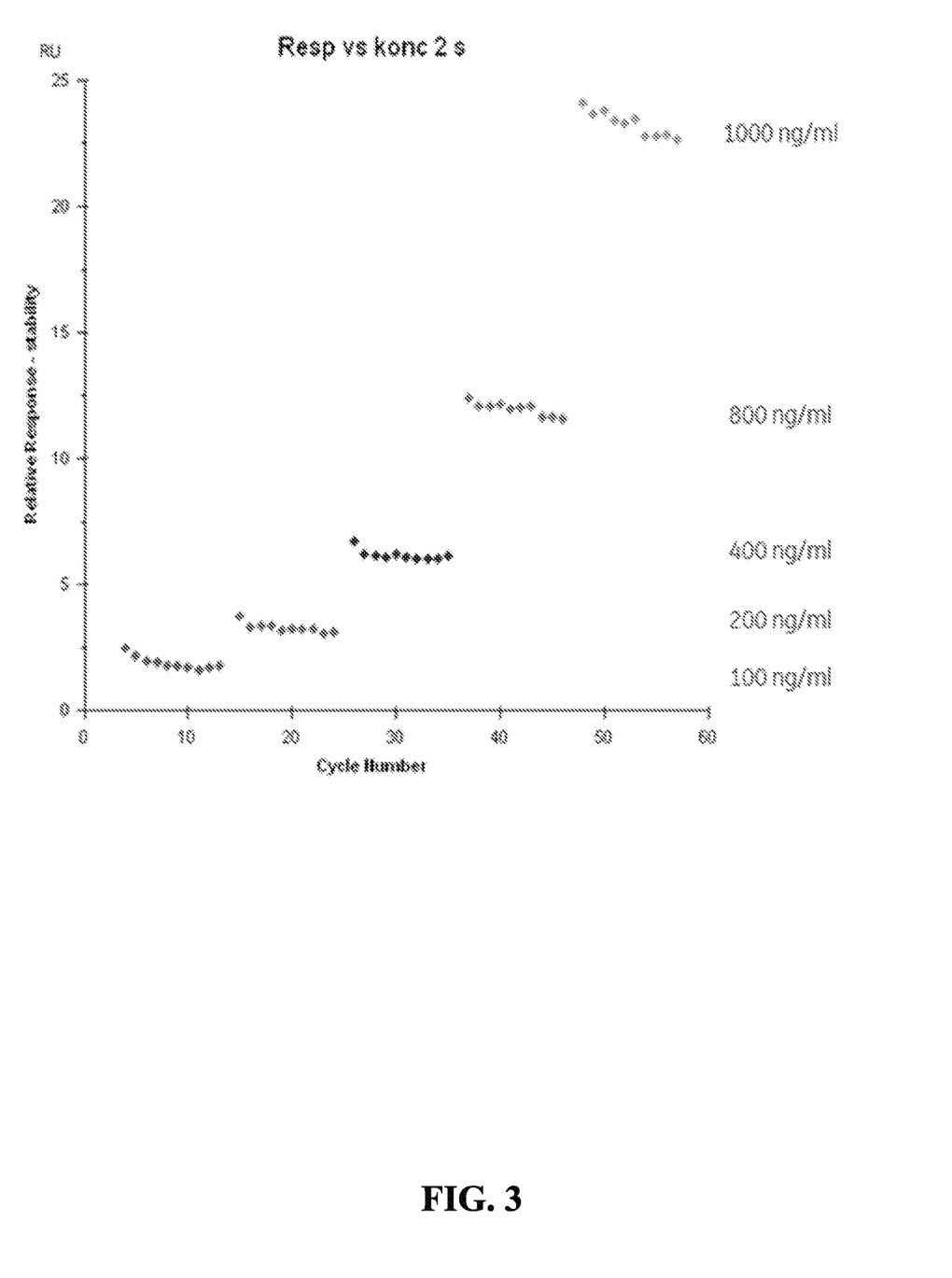
FIG. 3 shows the response after the injection versus cycle number.
Figure 4:
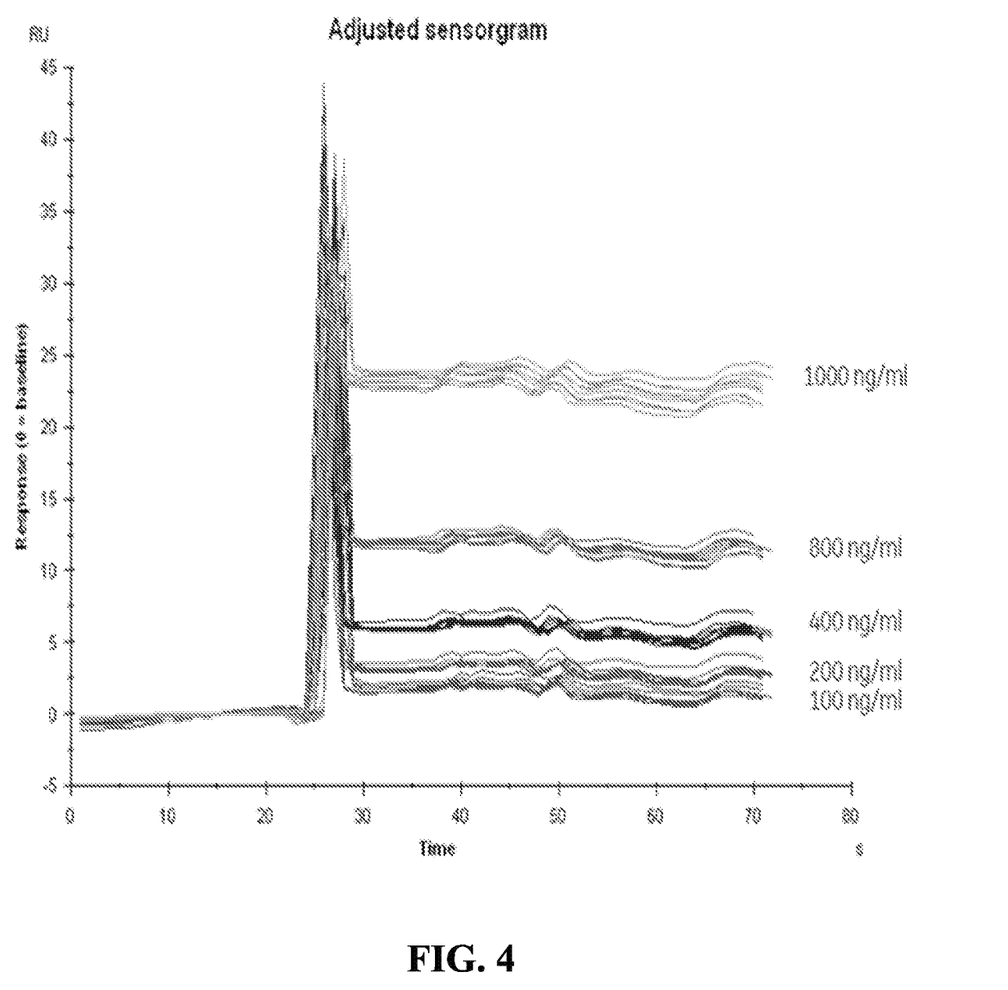
FIG. 4 shows the corresponding sensograms with cycle times when no commands are added to the injection.

The results of the above experiments are shown in FIG. 3 and FIG. 4. These figures demonstrate that a 2 second injection time is enough to detect a protein binder in a sample down to at least 100 ng/ml.

FIG. 3 shows the response after the injection versus cycle number, demonstrating that the responses are reproducible across multiple cycles for each concentration of analyte and that the relative responses reflect the increase in concentration of analyte. FIG. 4 shows the corresponding sensograms with cycle times when no commands are added to the injection. The data demonstrates that extremely short contact times can produce highly useful and repeatable information.

Figure 5:
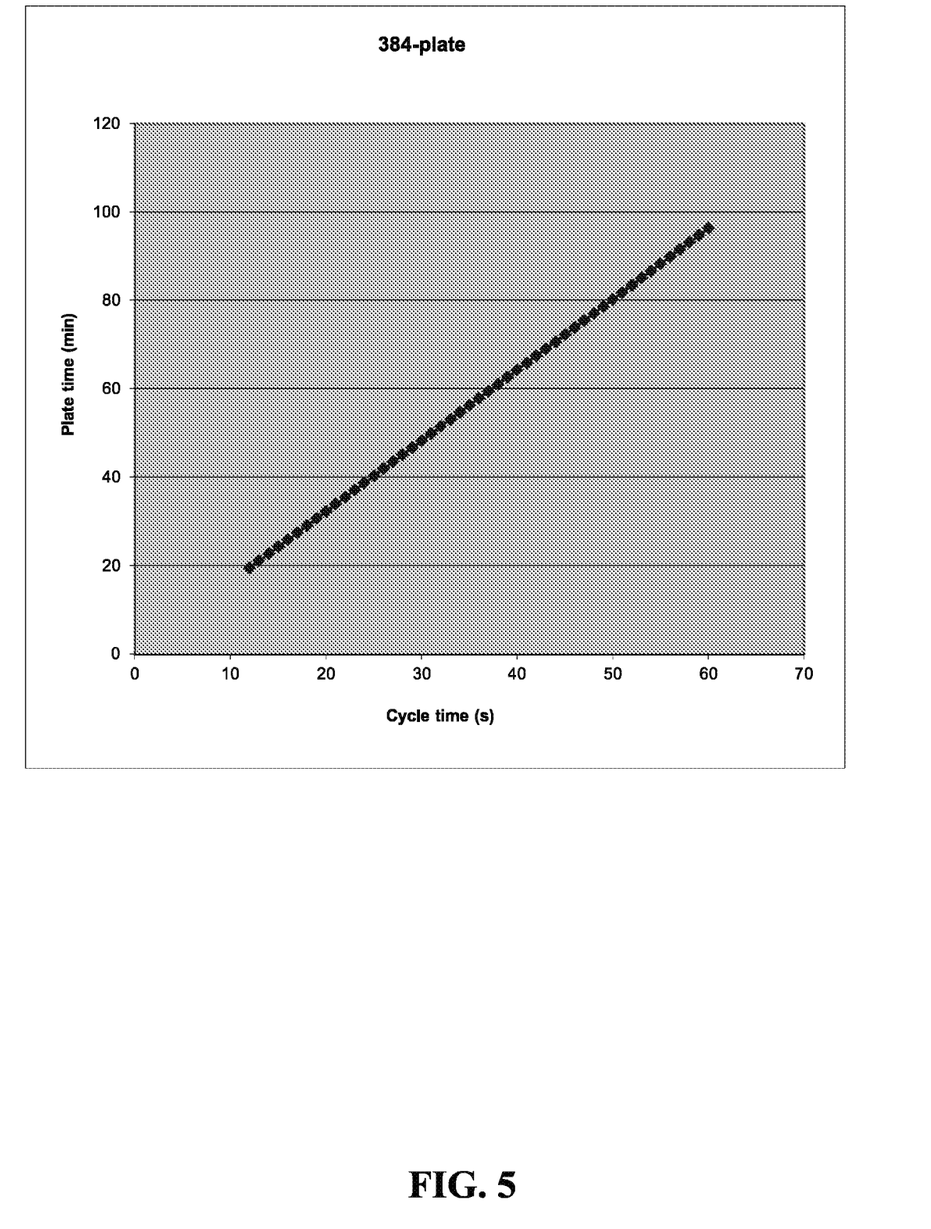
FIG. 5 shows graphically the time it takes to run a 384 plate with a 4-needle system at various times for each cycle.

FIG. 5 is an information plot showing the calculated total experiment time on a 384 well plate with a 4-needle system at various times for a given cycle. If a contact time of only 2 seconds is employed, and all other commands are avoided, the sample time can be significantly lowered. For example, a 12 seconds cycle time would allow a 4-needle system to run a 384 plate in under 20 minutes (96×12s).

The invention claimed is:

1. A computer program comprising program code means for operating a sensor device to detect an interaction between an analyte and a ligand on a sensor surface according to the following method when the program is run on a computer, the method comprising:
(a) providing a sensor surface having a ligand immobilized thereto wherein the ligand has a ligand density on the sensor surface configured to allow binding of analyte in a plurality of samples;
(b) flowing a first sample solution over the sensor surface, wherein the sample solution is contacted with the sensor surface for a contact time that is in the range of 0.1 to 15 seconds; and
(c) detecting the presence or absence of binding of a first analyte to the ligand on the sensor surface;
repeating steps (b) and (c) by flowing a subsequent sample solution that is the same or different than the first sample solution over the sensor surface to detect the presence or absence of binding between the ligand immobilized on the surface and a further analyte, the further analyte being the same or different than the first analyte, wherein the flowing of the second sample solution is initiated less than forty seconds after the flowing of the first sample solution over the sensor surface.

2. The computer program of claim 1, wherein the contact time is less than 10 seconds.

3. The computer program of claim 1, wherein the contact time is less than 5 seconds.

4. The computer program of claim 1, wherein the contact time is less than 3 seconds.

5. The computer program of claim 1, wherein the contact time is less than 2 seconds.

6. The computer program of claim 1, wherein detection at the sensor surface is based on evanescent wave sensing.

7. The computer program of claim 1, wherein detection at the sensor surface is based on surface plasmon resonance (SPR).

8. The computer program of claim 1, wherein the further analyte is the same as the first analyte.

9. The computer program of claim 1, wherein the further analyte is different to the first analyte.

10. The computer program of claim 1, wherein steps (b) and (c) are repeated for a third sample solution.

11. The computer program of claim 1, wherein steps (b) and (c) are repeated at least ten times to assay at least ten further solutions.

12. The computer program of claim 1, wherein the flowing of the second sample solution is initiated less than 15 seconds after the flowing of the first sample solution over the sensor surface.

13. The computer program of claim 1, wherein no regeneration step is carried out between initiating the flowing of at least one of the sample solutions over the sensor surface and initiating flowing of a next sequential sample solution over the sensor surface.

14. The computer program of claim 1, wherein no washing step and/or no carry-over control injection step is carried out between initiating the flowing of at least one of the sample solutions over the sensor surface and initiating flowing of a next sequential sample solution over the sensor surface.

15. The computer program of claim 1, wherein the ligand density on the sensor surface in a range 5000 RU to 50000 RU.

16. The computer program of claim 15, wherein the ligand density on the sensor surface is in a range 5000 RU to 15000 RU.

17. The computer program of claim 1, wherein step (c) comprises determining the analyte concentration in the sample solution.

18. The computer program of claim 1, wherein step (c) comprises determining the affinity of analyte to the ligand.

19. The computer program of claim 1, comprising determining differences in analyte concentrations and/or analyte affinities between different sample solutions.

20. The computer program of claim 1, wherein the ligand or analyte is an antibody or fragment thereof.

* * * * *